(12) United States Patent
Matton et al.

(10) Patent No.: US 12,377,267 B2
(45) Date of Patent: Aug. 5, 2025

(54) NON-INVASIVE WEARABLE DEVICE FOR ELECTRICAL NERVE STIMULATION

(71) Applicant: STIMULI TECHNOLOGY, Boulogne Billancourt (FR)

(72) Inventors: Yves Matton, Fontenay aux Roses (FR); Olivier Le Blainvaux, Le Chesnay (FR); Pierre Le Blainvaux, Boulogne Billancourt (FR); Tristan Martel, Montcaret (FR)

(73) Assignee: STIMULI TECHNOLOGY, Boulogne Billancourt (FR)

( * ) Notice: Subject to any disclaimer, the term of this patent is extended or adjusted under 35 U.S.C. 154(b) by 315 days.

(21) Appl. No.: 17/759,292

(22) PCT Filed: Jan. 19, 2021

(86) PCT No.: PCT/EP2021/050988
§ 371 (c)(1),
(2) Date: Jul. 22, 2022

(87) PCT Pub. No.: WO2021/148368
PCT Pub. Date: Jul. 29, 2021

(65) Prior Publication Data
US 2023/0079328 A1     Mar. 16, 2023

(30) Foreign Application Priority Data
Jan. 22, 2020 (FR) ...................................... 2000613

(51) Int. Cl.
*A61N 1/36* (2006.01)
*A61N 1/04* (2006.01)

(52) U.S. Cl.
CPC ....... *A61N 1/36007* (2013.01); *A61N 1/0456* (2013.01); *A61N 1/0484* (2013.01); *A61N 1/3603* (2017.08)

(58) Field of Classification Search
CPC .............. A61N 1/36007; A61N 1/0456; A61N 1/0484; A61N 1/3603; A61N 1/0487; A61N 1/0404; A61N 1/0412; A61N 1/0452
See application file for complete search history.

(56) References Cited

U.S. PATENT DOCUMENTS 6,505,079 B1 * 1/2003 Foster .................. A61N 1/3603
607/63
2014/0228927 A1 * 8/2014 Ahmad .............. A61N 1/36034
607/148

(Continued)

FOREIGN PATENT DOCUMENTS

WO     2018032105 A1    2/2018

OTHER PUBLICATIONS

PCT/EP2021/050988, International Search Report and Written Opinion, Mar. 3, 2021 (15 pages).

*Primary Examiner* — Paula J Stice
(74) *Attorney, Agent, or Firm* — FisherBroyles, LLP; Susan M. Oiler

(57) ABSTRACT

Portable non-invasive electrical nerve stimulation devices have an electrical one-piece module whose lower surface is configured to be applied to the outer surface of a human body. The one-piece module has a casing incorporating a pulse generator circuit connected to at least two electrodes preferably silicon-graphite electrodes, to deliver an electrical pulse to the nerve positioned in the human body through the electrodes. The one-piece module has a means of attachment to the human body. The means of attachment can be a single fastening system positioned on the upper part of an ankle, above the malleolus.

16 Claims, 3 Drawing Sheets

(56) References Cited

U.S. PATENT DOCUMENTS

| | | | |
|---|---|---|---|
| 2014/0303682 A1* | 10/2014 | Siff | A61N 1/0456 607/46 |
| 2016/0051817 A1* | 2/2016 | Popovic | G16H 20/30 607/72 |
| 2016/0346543 A1* | 12/2016 | Chen | A61N 1/36021 |
| 2017/0361091 A1* | 12/2017 | Tai | A61N 1/04 |
| 2018/0092550 A1* | 4/2018 | Sprenger | A61B 7/045 |
| 2019/0134393 A1* | 5/2019 | Wong | A61N 1/36025 |

\* cited by examiner

NON-INVASIVE WEARABLE DEVICE FOR ELECTRICAL NERVE STIMULATION

CROSS-REFERENCE TO RELATED APPLICATIONS

The present invention is filed under 35 U.S.C. § 371 as the U.S. national phase of International Patent Application No. PCT/EP2021/050988, filed Jan. 19, 2021, which designated the United States and which claims the benefit of French Patent Application No. 2000613 filed Jan. 22, 2020, which is hereby incorporated in its entirety including all tables, figures, and claims.

TECHNICAL FIELD

The present invention relates to the field of medical devices. More particularly, it relates to a portable non-invasive electrical nerve stimulation or transcutaneous electrical neurostimulation (TENS) device, particularly for tibial nerve stimulation and for treatment of over-active bladder.

Over-active bladder (OAB) is a condition in which the inner walls of the bladder tighten, regardless of how full it may be.

Over-active bladder affects approximately 17% of the world's population and is particularly common in elderly people.

The characteristic clinical signs of an over-active bladder are usually:
- frequent (or sometimes very frequent) urges to urinate, even if the bladder has not reached its maximum capacity (pollakiuria), which can lead to waking at night to urinate (nocturia);
- pressing need to use the toilet (urgency), with the apprehension of having to urinate at inconvenient times;
- bladder leakage and incontinence when the person is unable to go to the toilet or there is no toilet nearby.

Risk factors for over-active bladder include:
- urinary tract infection;
- presence of kidney stones;
- nervous system disorders; and
- increased consumption of caffeinated drinks.

There are several ways of limiting (or treating) the problem of over-active bladder:
- bladder re-education exercises to reduce the urge to urinate;
- specific medication to reduce the number of urges and limit leakage;
- an injection of botulinum toxin into the bladder muscle, allowing the bladder to hold more urine;
- stimulation, via an implant, of the sacral nerve, which is located in the pelvis and plays an important role in bladder management, or
- stimulation of the tibial nerve, which is located at the ankle and has branches close to the sacral nerve, thus allowing indirect stimulation of that nerve.

The tibial nerve is the medial terminal branch of the sciatic nerve. It is a mixed nerve, consisting of nerve fibres from the lumbar and sacral nerves. The tibial nerve first follows the median axis of the popliteal fossa and then, in the leg, descends medially to pass successively through the medial retro-malleolar region and the tarsal tunnel region. Usually, it divides in the tarsal tunnel into two terminal branches which join the sole of the foot: the medial plantar nerve and the lateral plantar nerve.

There is currently a need to develop and optimise techniques and treatments that will limit OAB.

Among the existing treatments, treatment by transcutaneous electrical neurostimulation of the tibial nerve appears to be an interesting and promising avenue.

PRIOR ART

Transcutaneous electrical neurostimulation is a non-medicinal and non-invasive technique designed specifically to relieve pain by means of a low-voltage electrical current transmitted by electrodes placed on the skin. The acronym TENS, by which this therapy is often referred to, derives from the expression "Transcutaneous Electrical Nerve Stimulation". The device that generates the desired current and to which the electrodes are connected is known as a "neurostimulator".

The electrodes, usually two or four in number, are attached to the skin using adhesive tape. They are placed near the painful area or, depending on the case, along the path of a specific nerve, usually the tibial nerve, or in other strategic locations. The person is encouraged to adjust the neurostimulator to find the intensity, frequency and duration of pulses that provide the most relief while causing the least discomfort.

The settings, as well as the duration and frequency of treatment sessions, can vary considerably from person to person. In some cases, the analgesic effect or pain relief is felt immediately, while in other cases 30 minutes or an hour of treatment may be needed before relief is achieved. For some people, the analgesic effect or relief disappears as soon as the treatment is stopped; for others, the relief may last for hours or even days.

As mentioned above, neurostimulators are particularly indicated for the prevention or treatment of over-active bladder (OAB), but may also be indicated for the prevention or treatment of anorectal disorders and perineal pain.

The term "anorectal disorders" refers to problems of transit that occur in the colon, such as constipation and faecal incontinence. Specifically, these disorders affect 39-66% of people with multiple sclerosis and have an impact on social activities for 1 in 6 people. Faecal incontinence and constipation can be experienced separately but more generally occur together. They are also frequently associated with urinary disorders.

Perineal pains are particularly difficult to treat, often requiring a multidisciplinary approach. Of these pains, pudendal, ilio-inguinal, ilio-hypogastric and genitofemoral neuralgia, pain with an osteoligamentary component, myofascial syndrome, and pain of muscular and venous origin, are becoming increasingly well identified.

Neuromodulation of the tibial nerve using an external neurostimulator has been shown to deliver painless, low-intensity electrical pulses along the path of the nerve, via electrodes stuck to the skin. Neuromodulation of the posterior tibial nerve involves stimulating the sensory afferents of this nerve; they belong to the same metameric territory as the sacral roots that control the vesico-sphincter system and anorectal system and carry the pain pathways of the perineum.

Today, there are various types of neurostimulators or devices for perineal electrostimulation. These include the Urostim 2™, marketed by Schwa-Medico™, to treat incontinence and strengthen the pelvic floor. This is a two-way device, which offers perineal electrotherapy. This can be achieved in different ways:
- perineal stimulation with a probe to strengthen the muscles of the perineum and relieve all types of incontinence (stress, urge or emergency, and mixed);

stimulation of the PTN (Posterior Tibial Nerve) by electrodes.

The Urostim 2™ is a rechargeable electrostimulation device that operates with a battery.

The stimulation threshold is determined by the patient's sensory perception of the stimulation. The stimulation parameters usually used for urinary and anorectal disorders are:

frequency 10 Hz, current 10-45 mA, intervals 200 microseconds.

Stimulation is carried out at home, by the patient, at a rate of 20-30 minutes per day for at least three months. The clinical outcome is assessed at the end of this period. If there is significant improvement, the stimulation can be continued.

The frequency can then be adapted on a case-by-case basis depending on the result (one session two to three times a week).

For this type of device, it is recommended that the stimulation session be carried out while resting, or in a sitting or lying position.

Other neurostimulators have been proposed. One example is the neurostimulator described in U.S. Pat. No. 9,254,382; this is a portable device that delivers stimuli to the ankle through specific electrodes. This device allows the physical activity of the bladder to be controlled a priori. The device described comprises a casing, a pulse generator circuit for generating an electro-acupuncture stimulus, and a strap for attaching the casing directly to the ankle. The device also includes a pair of D-shaped electrodes.

SUMMARY OF THE INVENTION

The present invention relates to the field of medical devices. More particularly, it relates to a portable non-invasive electrical nerve stimulation or transcutaneous electrical neurostimulation (TENS) device, particularly for tibial nerve stimulation and for treatment of over-active bladder.

Technical Problem

In view of the above, one problem that the present invention proposes to solve involves developing a new transcutaneous electrical neurostimulation device that has the advantage of being simple to use, easy to handle, compatible with the constraints of everyday life, and allows daily or almost daily stimulation of the tibial nerve over long periods (several hours) without posing an inconvenience to the patient. In particular, the device should help limit the discomfort associated with its use. In addition, it should be possible to use the device when the user is active and not just at rest, lying down or sitting.

Technical Solution

The solution to this problem has as its first aim a portable non-invasive electrical nerve stimulation device 1, comprising:

an electrical one-piece module 2 whose bottom surface 22 is designed to be applied to the outer surface 9 of a human body, the said module comprising a casing 3 incorporating a pulse generator circuit 4 connected to at least two electrodes 51, 52, preferably silicon graphite electrodes, the said electrodes being separated by a gap 50 of at least 50 mm to deliver an electrical pulse to the nerve positioned in the body; and a means 6 for attaching the said module 2 to the human body;

characterised in that the means of attachment 6 is a single fastening system positioned on the upper part of an ankle, above the malleolus.

Another aim of the invention is to use a device as per the invention for stimulation of nerves, preferably of the tibial nerve for the treatment of over-active bladder.

The invention also relates to a device as per the invention, for use in the prevention or treatment of over-active bladder through stimulation of the nervous system, preferably of the tibial nerve and more preferably of the posterior tibial nerve.

The invention also relates to a method of preventing or treating over-active bladder through stimulation of the nervous system by a portable non-invasive electrical nerve stimulation device according to the invention, preferably for stimulation of the tibial nerve and more preferably of the posterior tibial nerve.

The invention also relates to a method of controlling over-active bladder through stimulation of the nervous system by a portable non-invasive electrical nerve stimulation device as per the invention, preferably for stimulation of the tibial nerve and more preferably of the posterior tibial nerve.

The invention also relates to a kit suitable for implementing a control method as per the invention, comprising a device as described below, and preferably a user guide to administering the said electrical nerve stimulation.

Advantages Provided

In particular, the Applicant has been able to develop a portable, non-invasive electrical nerve stimulation device that has a small footprint and is lightweight and easy to use. In addition, the device advantageously has means of facilitating its use, including when the user is wearing shoes. The Applicant has been able to develop a device whose design allows it to be adapted to the wearing of low shoes, without however altering or limiting the neurostimulation. The user can therefore wear the device more easily, frequently and for long periods (several hours).

BRIEF DESCRIPTION OF THE DRAWINGS

The invention and the advantages arising from it will be better understood by reading the following description and non-limiting embodiments, illustrated with reference to the appended drawings in which.

DESCRIPTION OF EMBODIMENTS

In this description, unless otherwise specified, it is understood that when an interval is given, it includes the upper and lower limits of the said interval.

Figure 1:
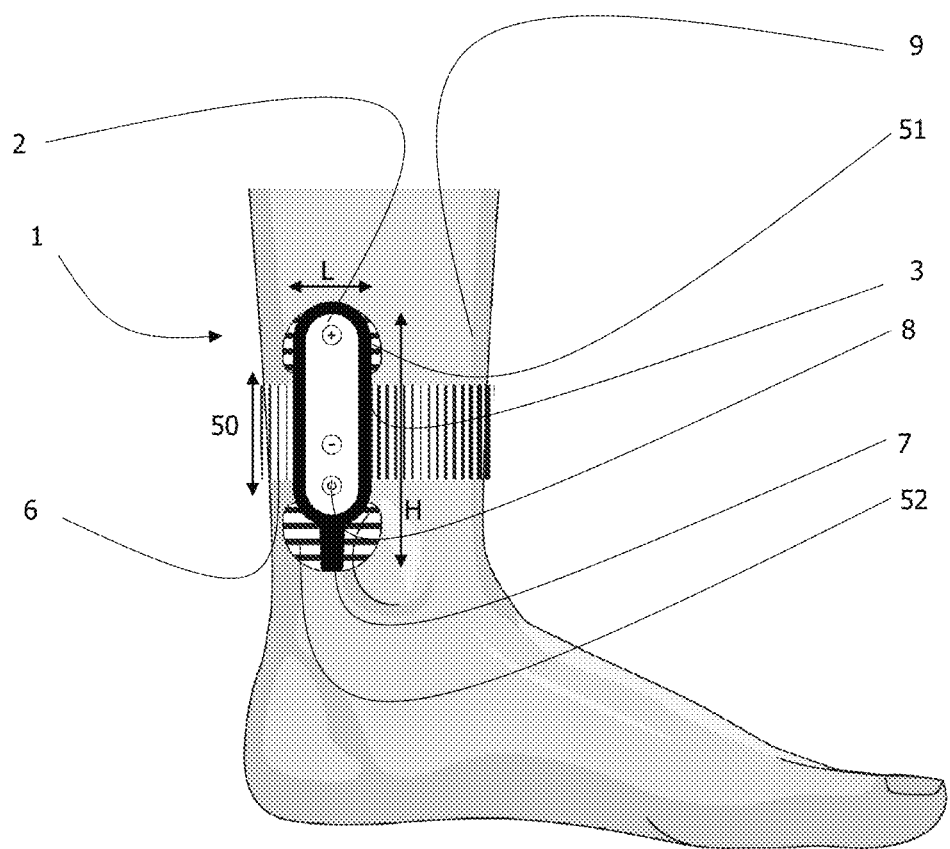
FIG. 1 shows a profile view of a users foot equipped with a device as per the invention.
Figure 2:
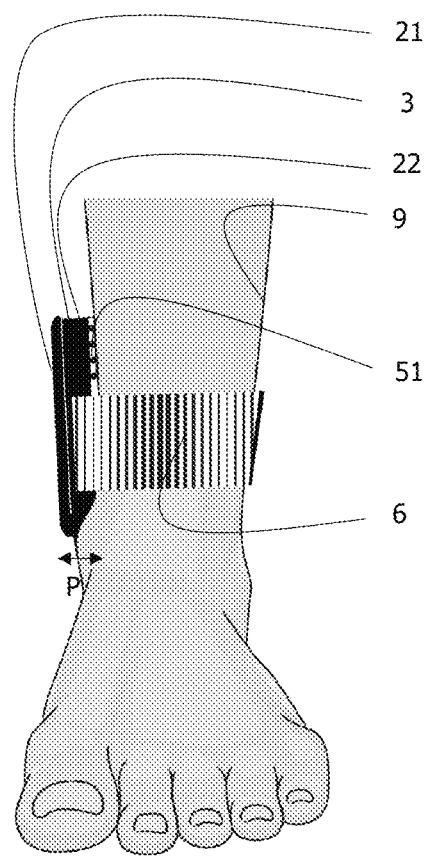
FIG. 2 shows a front view of a user's foot equipped with a device as per the invention.

As can be seen from FIGS. 1 and 2, the subject of the invention is a non-invasive portable device, that is, one that does not require any incision or invasion of the skin. The device is an electrical nerve stimulation device 1, also known as a neurostimulator. This is a device that generates a desired current at electrodes 51 and 52. The device is portable in that it can be carried easily, and is wireless, that is, not connected to a socket and free of visible wires that could be cut, broken or stripped during use. This is advantageous and guarantees safety in use.

The device 1 comprises an electrical one-piece module 2 with a top face 21 that includes one or more control buttons 8. Preferably, the device 1 includes at least one control button 8 on its upper surface 21 for switching the device on and off. The same button or an additional button can be used to adjust the intensity and/or duration of the treatment. This makes the device particularly ergonomic.

The bottom surface 22 of the one-piece module 2 is in turn adapted for application to the outer surface 9 of a human body. The lower surface 22 is applied preferably to the skin, and most preferably at the level of the tibial nerve, that is, on the upper part of the ankle, above the malleolus as shown in FIGS. 1 and 2.

The device 1 as per the invention comprises a casing 3 which incorporates a pulse generator circuit 4 connected to at least two electrodes 51, 52.

Preferably, the electrodes are integral with the product or the casing 3.

Figure 3:
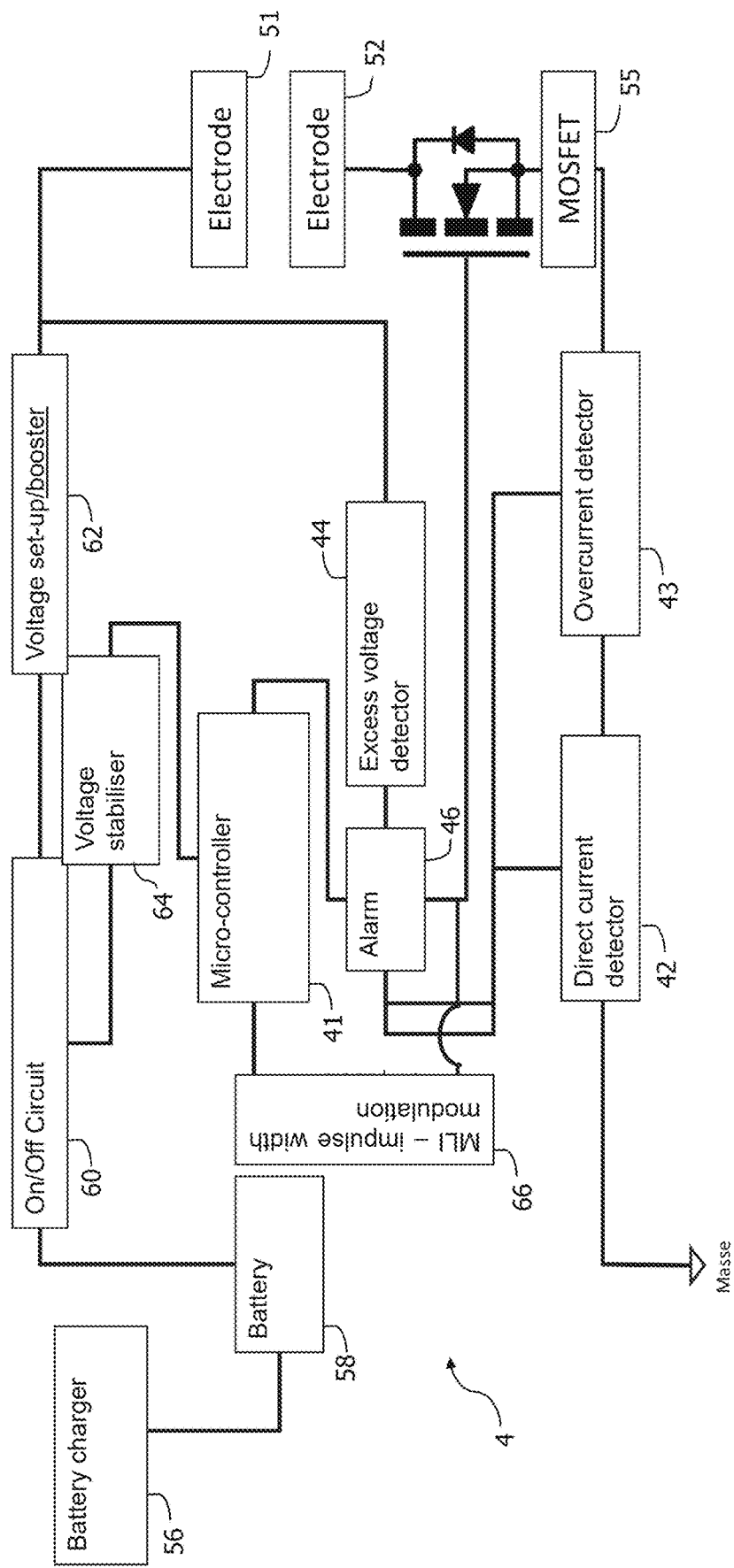
FIG. 3 shows a diagram of a pulse generator circuit of a device as per the invention.

As shown in FIG. 3, the circuit advantageously consists of different modules for delivering a current to the electrodes.

The circuit 4 preferably incorporates more than one of the following elements:
- a battery charger 56, which is preferably a micro-USB, USB or USB-C charger;
- a battery 58, which is for example a rechargeable battery of the nickel cadmium, nickel metal hydride, lithium Ion, lithium iron phosphate or lead type, preferably with an independent operating time of 24 hours or more or 20 hours or more;
- an on/off circuit 60;
- a voltage booster 62;
- a voltage stabilizer 64;
- a micro-controller 41 which allows the control of the stimulation parameters 66;
- an alarm 46;
- an excess voltage detector 44, with hardware function only;
- an earthed DC detector 42 with a hardware function only;
- an excess current detector 43, with hardware function only;
- an insulated gate field-effect transistor 55 (MOSFET) designed to close the circuit to trigger the stimulation; and is connected to the two electrodes 51, 52.

Preferably, the pulse generator circuit 4 of the device according to the invention comprises:
- a battery 58, which is for example, a rechargeable battery of the nickel cadmium, nickel metal hydride, lithium ion, lithium iron phosphate or lead type, preferably with a nominal operating time of 24 hours or more or 20 hours or more;
- a micro-controller 41;
- a direct current detector 42;
- an excess current detector 43;
- an excess voltage detector 44;
- an insulated gate field-effect transistor 55 (MOSFET); and optionally
- an alarm 46;
to stop the stimulation in case of malfunction.

Advantageously, the Applicant has integrated a microcontroller 41 into the pulse generator circuit 4 of the device according to the invention in order to increase the security of the device.

Furthermore, when a threshold voltage, threshold current or direct current is detected, a hardware safety device can advantageously stop the stimulation.

As illustrated in FIGS. 1-3, the pulse generator circuit 4 is connected to at least two electrodes 51, 52. Electrodes are elements capable of conducting electrical current, and are used to stimulate the nervous system, particularly the tibial nerve.

Preferably, the electrodes are non-adhesive. This prevents a sticky feel or appearance, which is uncomfortable for the user. Such non-adhesive electrodes thus allow more regular, better and more consistent use by the user.

The electrodes of the device according to the invention are preferably of silicone graphite. They are at positioned at least 50 mm apart and deliver an electrical impulse to the nerve positioned in the body, preferably the tibial nerve. Preferably, the electrodes 51, 52 are at least 70 mm apart, more preferably at least 80 mm apart and even more preferably at least 90 mm apart. Particularly advantageously, the distance between the two electrodes is between 50 and 150 mm, preferably between 75 and 125 mm and even more preferably between 80 and 100 mm.

In particular, the Applicant was able to demonstrate that it was not advisable to have a distance of less than 50 mm between the electrodes 51, 52 to effectively touch the tibial nerve.

The one-piece module advantageously includes, on its lower part, a stud 7 that allows the module casing 3 to be connected to a lower electrode 52, thus allowing free passage of the malleolus under the said device 1.

The presence of this stud allows the overall size of the device to be limited. Furthermore, this reduction in the size of the device allows the user to put on shoes or wear low shoes, while keeping the device above the ankle; it can then be worn for long periods of time (several hours). The device can thus be adapted to all ankle widths without the risk of hindering the user, for example by contact between a rigid part and the inner malleolus.

The user is therefore not obliged to take off footwear when using the device as per the invention, which is a neurostimulator.

The device as per the invention further includes a means of attachment 6 of the module 2 to the human body; this means is composed of a material selected from polyester, polyamide or rubber, used alone or in combination. As illustrated in FIGS. 1 and 2, the means of attachment 6 is a single fastening system positioned on the top of an ankle, above the malleolus.

Preferably, the means of attachment is a single strap or single band adapted so that the electrodes 51, 52 of the module are in direct contact with the skin of the human body 9 when the device is positioned on the body.

Alternatively, the means of attachment 6 may also take the form of an armband.

Advantageously, the device includes at least one control knob 8 on its upper surface 21 for adjusting the power, intensity and/or duration of the treatment.

The intensity of the treatment generally varies between 0 and 150 mA; preferably it is between 0 and 50 mA, and more preferably it is between 10 and 45 mA.

The preferred form of stimulation or signal is a phase form. The stimulation or pulse frequency is between 5 and 30 Hz, preferably between 10 and 20 Hz.

The pulse width or pulse duration is generally between 50 and 300 microseconds, preferably between 150 and 250 microseconds and more preferably between 150 and 200 microseconds.

Advantageously, the pulse duration can be modulated by pulse width modulation (PWM).

Finally, the stimulation time per day is between 1 minute and 24 hours, preferably between 10 minutes and 22 hours, and more preferably between 20 minutes and 20 hours.

Advantageously, the device as per the invention comprises a one-piece module 2, composed of a material chosen from silicone rubber, acrylonitrile butadiene styrene, styrene-ethylene-ethylene-propylene-styrene block copolymer, polycarbonate taken alone or in combination; and silicone-graphite electrodes 51, 52.

Advantageously, the device as per the invention integrates a wireless digital data exchange module, whose wireless network implements a standard of the 802.11, Bluetooth or DECT type.

In particular, the wireless digital data exchange module allows remote and on-demand activation.

Alternatively, the device as per to the invention may advantageously be an item connected to the Internet and fall under the term "Internet of things" (IoT). This term refers to a growing number of objects that are connected to the Internet and allow communication between our so-called physical assets and their digital existence. The network must be capable of sending very small messages over long distances without necessarily using mobile network systems and with low energy consumption.

Advantageously, the overall volume of the electrical one-piece module 2 of the device as per the invention is less than 90 cm3, preferably less than 75 cm3, and even more preferably less than 70 cm3.

More particularly, the device as per the invention advantageously has the following characteristics:
- the height (H) of the electrical one-piece module 2 is less than 150 mm and preferably less than 100 mm;
- the width (L) of the electrical one-piece module 2 is less than 40 mm and preferably less than 30 mm;
- the depth (P) of the electrical one-piece module 2 is less than 15 mm and preferably less than 10 mm.

The device as per the invention is a neurostimulator which as such allows transcutaneous electrical neurostimulation, more commonly known as "TENS" (Transcutaneous Electrical Nerve Stimulation). The use of the device is therefore a non-medicinal and non-invasive technique that can relieve pain or prevent or treat certain disorders such as over-active bladder (OAB) as well as anorectal disorders and perineal pain.

The device can therefore be used in particular:
- on one hand, to inhibit the pain signal: the device as per the invention generates electrical impulses which activate nerve fibres that are larger and faster than those used to convey the pain. A message is transmitted to the brain via the spinal cord, thus masking the pain signal throughout the stimulation session;
- on the other hand, for endorphin stimulation, which favours increased production of endorphins. This increase produces a general analgesic effect. TENS in endorphin mode is characterised by a sensation of small pulses.

TENS programmes offer one or the other of these mechanisms of action or a combination of both. The type of programme and the positioning of the electrodes are determined during a test session with a health professional. The choice is made according to the feelings of each patient.

The device as per the invention is a miniaturised lightweight device; its design allows it to be attached to many parts of the body via the single strap, which can act as a strap or an armband. The device is compact and can easily be concealed under clothing, preferably loose-fitting clothing (trousers, shirt etc). It allows normal movement and quality of life without worrying about the size of the device.

This is a personal medical device that can be used at any time of the day for varying periods of time, depending on the episodes.

Preferably, the electrodes of the device are positioned over the medial malleolus and deliver an electrical pulse to the posterior tibial nerve.

This invention will now be illustrated with the following examples.

EXAMPLES

Example 1: Comparison and Test Use of Device as Per the Invention Initial Version or TENSI+ Improved Version Intensity: 0-50 mA
Form of stimulation: phase
Phase length: 150-200 microseconds
Stimulation frequency: 10-20 Hz
Duration of stimulation per day: 20 minutes to 20 hours
The device circuit includes the following elements:
- a battery charger, preferably a micro-USB, USB or USB-C charger;
- a battery, which is for example a rechargeable battery of the nickel cadmium, nickel metal hydride, lithium ion, lithium iron phosphate or lead type with a nominal operating time of 24 hours and preferably more than 20 hours;
- an on/off circuit;
- a voltage booster;
- a voltage stabiliser;
- a micro-controller 41 which allows the control of the stimulation parameters;
- an alarm 46;
- an excess voltage detector 44, with hardware function only;
- an earthed DC detector 42 with a hardware function only;
- an excess current detector 43, with hardware function only;
- an insulated gate field-effect transistor (55) (MOSFET—Metal Oxide Semiconductor Field Effect Transistor) for closing the circuit to trigger the stimulation;
- and is connected to two electrodes 51, 52.

The TENSI+ model also includes a stud 7 for connecting the module casing 3 to a lower electrode 52, thus allowing the malleolus to pass freely under the device as per the invention.

Tab. 1. The results of the comparison are shown in Table 1 below.

TABLE 1

| Design assessed | Urostim 2.0 | Initial design | TENSI+ design |
|---|---|---|---|
| Operation of the product is simple and intuitive | 3.1 | 3.2 | 4.1 |
| The product is easy to install | 2.6 | 2.7 | 4.0 |
| The product is comfortable to wear | 1.9 | 2.1 | 4.0 |
| I can wear the device every day at home (20-30 min) | 2.7 | 3.6 | 4.1 |
| I can wear shoes with the device | 1.7 | 2.6 | 4.0 |
| There is no stigma with this device | 1.6 | 3.6 | 3.8 |
| Average | 2.23 | 2.94 | 3.98 |

Score from 1 (not at all) to 5 (very much so) for each question Conclusion:

Three devices were evaluated by a group of 20 participants to rate, on a scale of 1 to 5 (1=not at all and 5=very much so), the ease of use and ergonomics of the three products.

These three devices are the following:

Urostim 2.0: device already on the market;

Initial design: first version of the device as per the invention;

TENSI+: the latest improved version of the device according to the invention including a stud that allows easier passage of the malleolus.

A series of questions were asked of users who tested these devices over several days.

The devices as per the invention clearly appear to have advantages over the prior art.

In particular, the TENSI+ device has the highest average score for each of the questions asked of the users.

The devices as per to the invention in general, and more particularly the TENSI+ device, appear to be the most practical and to present an ease of use greater than that of the prior art thanks to a reduced size that allows wearing of shoes, without modifying or limiting the neurostimulation. Furthermore, the devices as per the invention can be used daily over long periods (several hours) by the user while resting or during activity, while remaining comfortable to wear.

The invention claimed is:

1. A portable, non-invasive electrical nerve stimulation device, comprising:
    an electrical one-piece module having a lower surface configured to be applied to an outer surface of a human body, the one-piece module comprising a casing incorporating a pulse generator circuit connected to at least two electrodes, the at least two electrodes being separated from one another by a gap of at least 50 mm and aligned with one another to deliver an electrical pulse to a tibial nerve of the human body;
    a stud extending from a first end of the casing and operatively connectable to a first electrode of the at least two electrodes, wherein the stud is configured to position the first electrode in a caudal position along the tibial nerve below the malleolus; and
    a single fastening system cooperating with the casing and configured to be positioned on an upper part of an ankle of a user with the stud below the malleolus and configured to orient a second electrode of the at least two electrodes in a cranial position along the tibial nerve, relative to the first electrode, above the malleolus.

2. The device according to claim 1, wherein the single fastening system comprises:
    a single strap or a single band, made of a material selected from the group consisting of polyester, polyamide, rubber, and combinations thereof; and
    adapted so that the electrodes of the module are in direct contact with skin of the human body when the device is positioned on the human body.

3. The device according to claim 1, comprising at least one control button on an upper surface.

4. The device according to claim 1, wherein the one-piece module consists of a material selected from the group consisting of silicone rubber, acrylonitrile butadiene styrene, styrene-ethylene-ethylene-propylene-styrene block copolymer, polycarbonate, and combinations thereof; and silicone-graphite electrodes.

5. The device according to claim 1, wherein the pulse generating circuit includes:
    a battery;
    a micro-controller;
    a direct current detector;
    an excess current detector;
    an excess voltage detector; and
    an insulated gate field-effect transistor;
wherein the micro-controller is configured to stop the electrical pulse in case of detection of an excess current or an excess voltage.

6. The device of claim 5, wherein the battery is a rechargeable battery of nickel cadmium, nickel metal hydride, lithium ion, lithium iron phosphate, or lead type.

7. The device of claim 5, wherein the insulated gate filed effect field-effect transistor comprises a metal oxide semiconductor filed field effect transistor.

8. The device of claim 5, wherein the pulse generating circuit further comprises an alarm.

9. The device according to claim 1, wherein an overall volume of the electrical one-piece module is less than 90 000 mm$^3$.

10. The device according to claim 1, wherein:
    a height (H) of the electrical one-piece module is less than 150 mm;
    a width (L) of the electrical one-piece module is less than 40 mm;
    a depth (P) of the electrical one-piece module is less than 15 mm.

11. The device of claim 1, wherein the single fastening system is oriented perpendicular to the at least two electrodes.

12. The device of claim 1, wherein the single fastening system connects to the casing at a position between the first electrode and the second electrode.

13. The device of claim 1, wherein each of the at least two electrodes is a silicon graphite electrode.

14. The device of claim 1, wherein each of the at least two electrodes are non-adhesive electrodes.

15. A method of treating over-active bladder through stimulation of a nervous system, by providing a portable, non-invasive electrical nerve stimulation device according to claim 1 configured for a patient to attach to one of the patient's ankles at a position above the malleolus.

16. The method according to claim 15, wherein the device is configured to stimulate a posterior tibial nerve.

* * * * *